US00PP14960P2

(12) United States Plant Patent
Bergman

(10) Patent No.: US PP14,960 P2
(45) Date of Patent: Jun. 29, 2004

(54) CHRYSANTHEMUM PLANT NAMED 'DARK YOELMIRA'

(50) Latin Name: *Chrysanthemum×morifolium*
Varietal Denomination: Dark Yoelmira

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/676,785

(22) Filed: Oct. 1, 2003

(51) Int. Cl.[7] ..... A01H 5/00

(52) U.S. Cl. ..... Plt./292

(58) Field of Search ..... Plt./292

*Primary Examiner*—Anne Marie Grunberg
*Assistant Examiner*—Annette H Para
(74) *Attorney, Agent, or Firm*—C. A. Whealy

(57) ABSTRACT

A distinct cultivar of Chrysanthemum plant named 'Dark Yoelmira', characterized by its uniform, compact and somewhat outwardly spreading plant habit; strong and freely branching growth habit; small dark green-colored foliage; uniform flowering response and habit; early flowering habit; numerous small decorative-type inflorescences; purple-colored ray florets; and good postproduction longevity with plants maintaining good substance and color for about three or four weeks in an interior environment.

2 Drawing Sheets

Botanical classification/cultivar designation: *Chrysanthemum×morifolium* cultivar Dark Yoelmira.

BACKGROUND OF THE INVENTION

The present Invention relates to a new and distinct cultivar of Chrysanthemum plant, botanically known as *Chrysanthemum×morifolium* and hereinafter referred to by the name 'Dark Yoelmira'.

The new Chrysanthemum is a product of a planned breeding program conducted by the Inventor in Fort Myers, Fla. The objective of the program is to create or discover new potted Chrysanthemum cultivars that are suitable for year-round production with uniform plant growth habit, good vigor and strong branching habit, numerous inflorescences, desirable inflorescence form and floret colors, fast and uniform flowering response, and good postproduction longevity.

The new Chrysanthemum is a naturally-occurring whole plant mutation of the Chrysanthemum cultivar Yoelmira, disclosed in U.S. Plant Pat. No. 12,514. The new Chrysanthemum was discovered and selected by the Inventor as a single flowering plant from within a population of flowering plants of Yoelmira in February, 2000, in a controlled environment in Fort Myers, Fla. The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new Chrysanthemum by vegetative tip cuttings was first conducted in Fort Myers, Fla. in May, 2000. Asexual reproduction by cuttings has shown that the unique features of this new Chrysanthemum are stable and reproduced true to type in successive generations.

SUMMARY OF THE INVENTION

The cultivar Dark Yoelmira has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Dark Yoelmira'. These characteristics in combination distinguish 'Dark Yoelmira' as a new and distinct Chrysanthemum:

1. Uniform, compact and somewhat outwardly spreading plant habit.
2. Strong and freely branching growth habit.
3. Small dark green-colored foliage.
4. Uniform flowering response and habit.
5. Early flowering, 8-week response time.
6. Numerous small decorative-type inflorescences.
7. Purple-colored ray florets.
8. Good postproduction longevity with plants maintaining good substance and color for about three or four weeks in an interior environment.

Plants of the new Chrysanthemum differ primarily from plants of the cultivar Yoelmira primarily in ray floret coloration as plants of the cultivar Yoelmira have light lavender-colored ray florets. In addition, plants of the new Chrysanthemum are more vigorous and flower about one or two days later than plants of the cultivar Yoelmira.

Plants of the new Chrysanthemum differ from plants of the cultivar Apricot Yoelmira, disclosed in a U.S. Plant Patent application filed concurrently, primarily in ray floret coloration as plants of the cultivar Apricot Yoelmira have apricot bronze-colored ray florets. In addition, plants of the new Chrysanthemum typically produce a small amount of pollen whereas plants of the cultivar Apricot Yoelmira do not produce pollen.

Plants of the new Chrysanthemum can be compared to plants of the cultivar Yellow Yoelmira, disclosed in U.S. Plant Pat. No. 12,529. In side-by-side comparisons conducted in Fort Myers, Fla., plants of the new Chrysanthemum differed from plants of the cultivar Yellow Yoelmira in the following characteristics:

1. Plants of the new Chrysanthemum were more vigorous than plants of the cultivar Yellow Yoelmira.
2. Plants of the new Chrysanthemum flowered one or two days later than plants of the cultivar Yellow Yoelmira.
3. Ray florets of plants of the new Chrysanthemum were apricot bronze in color whereas ray florets of plants of the cultivar Yellow Yoelmira were yellow in color.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of typical flowering plants of 'Dark Yoelmira'.

The photograph on the second sheet comprises a close-up view of typical inflorescences of 'Dark Yoelmira'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercially potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Dark Yoelmira.

Commercial classification: Decorative-type potted Chrysanthemum.

Parentage: Naturally-occurring whole plant mutation of Yoelmira, disclosed in U.S. Plant Pat. No. 12,514.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted Chrysanthemum that is typically grown as a natural spray-type. Uniform and compact plant form with lateral branches somewhat outwardly spreading; uniformly mounded crown. Strong and freely branching growth habit; about five lateral branches develop after removal of terminal apex (pinching); dense and full plants.

*Plant height.*—About 23.5 cm.

*Plant width.*—About 28 cm.

*Lateral branches.*—Length: About 20 cm. Diameter: About 5 mm. Internode length: About 1.4 cm. Strength: Strong. Texture: Pubescent. Color: 144A to 146A.

*Foliage description.*—Arrangement: Alternate; simple. Length: About 4.7 cm. Width: About 3.4 cm. Apex: Mucronate. Base: Truncate. Margin: Palmately lobed, sinuses between lateral lobes parallel to divergent. Texture, upper and lower surfaces: Pubescent. Color: Developing foliage, upper surface: More green than 147A. Developing foliage, lower surface: More green than 147B. Fully expanded foliage, upper surface: More green than 147A. Fully expanded foliage, lower surface: Lighter than 147B. Venation, upper surface: Closest to 147A. Venation, lower surface: 147B. Petiole length: About 2.3 cm. Petiole diameter: About 1.5 mm. Petiole color, upper and lower surfaces: 147B.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant. Plants are typically grown as natural spray-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about three to four weeks in an interior environment.

*Quantity of inflorescences.*—About eight inflorescences per lateral branch.

*Inflorescence bud.*—Height: About 5.5 mm. Diameter: About 7.5 mm. Shape: Oblate. Color: Closest to 146A.

*Inflorescence diameter.*—About 3.2 cm.

*Inflorescence depth (height).*—About 1.6 cm.

*Diameter of disc.*—About 4 mm.

*Receptacle diameter.*—About 3.5 mm.

*Ray florets.*—Shape: Elongated oblong. Orientation: Mostly upright. Aspect: Flat to arching. Length: About 1.6 cm. Corolla tube length: About 4 mm. Width: About 5 mm. Apex: Emarginate. Base: Fused into a corolla tube. Margin: Entire. Texture: Smooth, glabrous, satiny. Number of ray florets per inflorescence: About 115 arranged in numerous whorls. Color: When opening, upper and lower surfaces: 77A. Fully opened, upper surface: 155D overlain with 77A. Fully opened, lower surface: 155D underlain with 77A.

*Disc florets.*—Arrangement: Massed at center of receptacle. Shape: Tubular, elongated. Apex: Five-pointed. Length: About 6 mm. Diameter, apex: About 1.5 mm. Diameter, base: About 1 mm. Number of disc florets per inflorescence: About 7. Color: Immature: Close to 154C. Mature: Apex: Close to 9A. Mid-section and base: Close to 155D.

*Phyllaries.*—Quantity per inflorescence: About 52. Length: About 5 mm. Width: About 2 mm. Shape:

Deltoid. Apex: Acute. Base: Truncate. Margin: Entire. Texture, upper surface: Waxy, smooth. Texture, lower surface: Pubescent. Color, upper surface: Close to 146A. Color, lower surface: Close to 146A to 146B.

*Peduncles.*—Length: First peduncle: About 2 cm. Fourth peduncle: About 3.5 cm. Seventh peduncle: About 4.5 cm. Diameter: About 1.5 mm. Angle to vertical: About 50° from vertical. Strength: Strong, flexible. Texture: Pubescent. Color: 146A.

*Reproductive organs.*—Androecium: Present on disc florets only. Anther color: Close to 9A. Pollen amount: Scarce. Pollen color: 12A. Gynoecium: Present on both ray and disc florets. Style color: Close to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Dark Yoelmira', as illustrated and described.

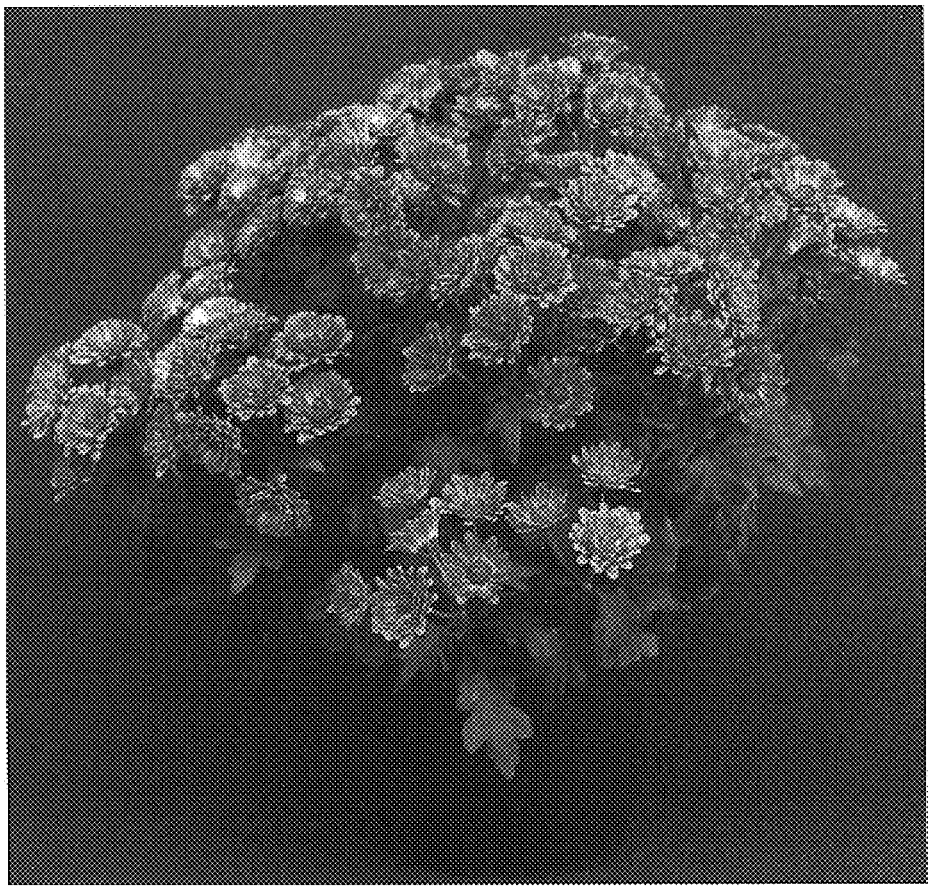

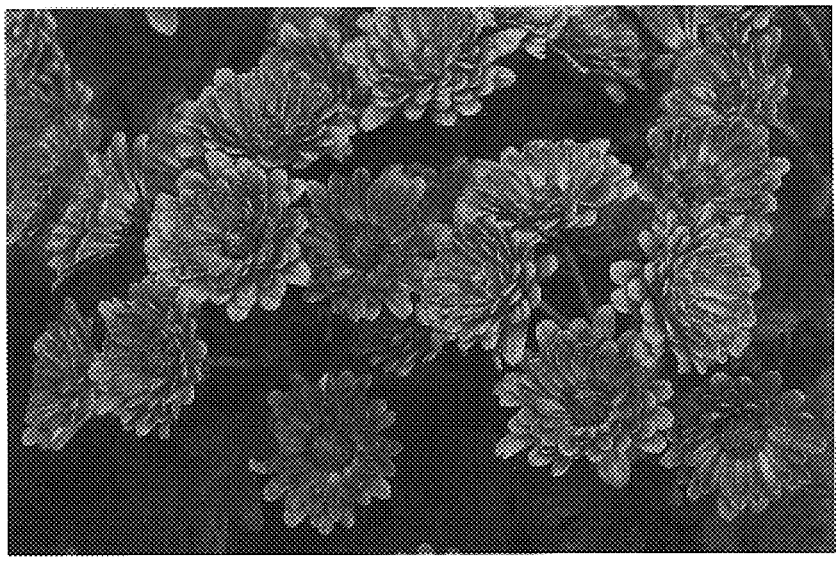

* * * * *